United States Patent [19]

Mackles

[11] Patent Number: 4,752,465
[45] Date of Patent: * Jun. 21, 1988

[54] AEROSOL FOAM

[75] Inventor: Leonard Mackles, New York, N.Y.

[73] Assignee: Product Resources International, Inc., New York, N.Y.

[*] Notice: The portion of the term of this patent subsequent to Jan. 27, 2004 has been disclaimed.

[21] Appl. No.: 5,597

[22] Filed: Jan. 21, 1987

Related U.S. Application Data

[63] Continuation-in-part of Ser. No. 778,026, Sep. 20, 1985, Pat. No. 4,639,367, which is a continuation-in-part of Ser. No. 713,294, Mar. 18, 1985, abandoned.

[51] Int. Cl.$^4$ ................................................ A61K 9/00
[52] U.S. Cl. .................................... 424/45; 514/945
[58] Field of Search ........................... 424/45; 514/945

[56] References Cited

U.S. PATENT DOCUMENTS

| | | | |
|---|---|---|---|
| 3,135,658 | 6/1964 | Hanus et al. | 424/45 |
| 3,419,658 | 12/1968 | Sanders | 424/45 |
| 3,770,648 | 11/1973 | Mackles | 252/305 |
| 3,849,580 | 11/1974 | Sejpal et al. | 426/116 |
| 3,929,985 | 12/1975 | Webb, Jr. | 424/45 |
| 4,174,295 | 11/1979 | Bargigia et al. | 252/305 |
| 4,188,412 | 2/1980 | Sejpal | 426/609 |
| 4,224,319 | 9/1980 | Marcadet | 424/238 |
| 4,425,164 | 1/1984 | Bliznak et al. | 106/211 |
| 4,639,367 | 1/1987 | Mackles | 424/45 |

FOREIGN PATENT DOCUMENTS 933486 10/1961 United Kingdom .
1121358 10/1966 United Kingdom .

*Primary Examiner*—Leonard Schenkman
*Attorney, Agent, or Firm*—Amster, Rothstein & Ebenstein

[57] ABSTRACT

A stable, edible anhydrous aerosol foam comprises a foamable liquid oil, a foaming agent, a food grade propellant, and at least 15 wt % dispersed solid particles. The foam is a stable whip having the consistency of whipped cream and can be dispensed in repeatable and measurable quantities onto a spoon. It is useful to dispense a wide variety of active, especially therapeutic, agents and, in particular, as an alternative to tablets or capsules which are hard to swallow or liquid medicines having a bad taste.

18 Claims, No Drawings

AEROSOL FOAM

RELATED APPLICATIONS

This application is a continuation-in-part of U.S. patent application Ser. No. 778,026, filed Sept. 20, 1985, now U.S. Pat. No. 4,639,367 which is in turn a continuation-in-part of U.S. patent application Ser. No. 713,294, filed Mar. 18, 1985, now abandoned.

BACKGROUND OF THE INVENTION

Tablets and capsules are the most common dosage forms for the oral administration of nutritional, medicinal, or other therapeutic products. It is well known, however, that these dosage forms are unacceptable for use by people who have difficulty in swallowing tablets and capsules and that the difficulty is exacerbated by larger tablets and capsules and, in some instances, by the bad taste of the medication. It is generally accepted that these types of problems with medications are serious because they may lead to a failure on the part of patients to comply with the medication regimen ordered by the physician.

The common alternatives to conventional tablets and capsules are chewable tablets and aqueous or hydroalcoholic liquids such as syrups, suspensions and elixirs. Such dosage forms are commonly used for analgesics, cough and cold medications, antibiotics, vitamins and many other nutritional or medicinal products. In general, these forms do not significantly improve the taste of a medication or make it easier to swallow larger doses. For example, therapeutic agents in either chewable tablet or suspension form are generally disliked because they are gritty, astringent and leave an unpleasant aftertaste. Oils, such as mineral oil, fish oils, cod liver oil and castor oil, are usually taken in large doses and, since they are greasy and unpleasant to take, some method must be found to make them easier to ingest. In the past this problem has been dealt with by encapsulating the oils in soft gelatin capsules or by emulsifying the oils in oil-in-water emulsions. These solutions have not been completely satisfactory.

The problem with encapsulation is that, since the maximum size soft capsule that can be ingested contains only about one gram of oil, the ingestion of many such capsules is required when the dose of the oil is large. In the case of fish oil the dose is about five grams a day or more, and the doses of cod liver oil, castor oil, and mineral oil are even larger. The problem with emulsification is that bottles of oil-in-water emulsions of oils are subject to deterioration as a result of attack by microorganisms or oxidation by the air to which they are continually exposed and thus have a limited shelf life. Oils and oil-soluble active agents are frequently vulnerable to oxidation. The integrity of oils, such as fish oil containing Omega 3 fatty acids, and the vitamin potency and unsaturated fatty acid character of oils, such as fish liver oils, are all susceptible to attack by oxidation.

Although aerosol packaging has found high consumer acceptance in many areas, including pharmaceutical products such as inhalants, it has not heretofore been considered for use in formulations requiring a high concentration of suspended solids, i.e., greater than 5 to 13%, because a high solids content usually causes malfunctioning of the aerosol valve. It is neither economical nor practical to dispense active solid agents in the very dilute formulations which would be required for dispensing through an aerosol valve. Moreover, such dilute formulations usually produce an uncontrollable and unmeasurable spray, thereby making it difficult to control or measure the amount of the formulation being dispensed. A further difficulty with aerosol packaging is that most aqueous aerosol solutions would be unacceptable for dispensing active solid agents because the dissolution of the active ingredient prior to ingestion could reduce its bio-availability and also produce an unpleasant taste.

British Pat. No. 1,121,358 discloses an aerosol foam composition for dispensing an oral medication, but is specifically limited to compositions which are oil-in-water emulsions. Furthermore, the composition is either devoid of dispersed solid particles or contains a very minimal solids content, less than one percent. It is believed that the presence of water in the emulsion not only reduces the ability of the composition to hold particulate solids, but also introduces stability problems resulting in shorter shelf life.

There are several prior art patents which presumably disclose anhydrous aerosol foams. For example, U.S. Pat. No. 3,135,658 teaches a method of treating bovine mastitis with a medicated, pressurized, self-propelling, milk-miscible oleaginous liquid composition which foams only after it enters the udder and contacts the natural foaming agents of the milk. It does not teach any type of dosable or meterable foam. Furthermore, the composition is inedible or at least unpalatable.

U.S. Pat. No. 3,770,648 discloses an anhydrous aerosol foam composition for external use which incorporates a silicone resin in a solution of organic solvents to produce a stable "quick breaking" foam when the foam is rubbed into or spread over a surface on which it has been deposited. This patent does not disclose any anhydrous foam products which are suitable for ingestion. It also does not teach any type of dosable or meterable foam for dispensing high concentrations of solid therapeutic agents.

U.S. Pat. No. 3,849,580 discloses an aerosol dispensing system which delivers non-aqueous butter-like edible fat compositions in a foam form. These foams contain no foaming agent and are intended to be used as food spreads.

U.S. Pat. No. 3,929,985 teaches a medicated aerosol foam composition for introduction into the vagina for the treatment of vaginitis, but the composition is devoid of any dispersed solid particles and is inedible or at least unpalatable.

U.S. Pat. No. 4,425,164 teaches the preparation of an aerosol spray cookware lubricant composition similar to the product which is commercially available in food stores under the trademark "PAM". This spray is formed from a mixture of a vegetable oil solution of an emulsifier (lecithin) in admixture with at least 10%, preferably 20 to 30%, of a hydrocarbon propellant and up to 15%, preferably 3 to 10%, of suspended flour or starch particles. The resulting product is a spray in which the particles serve as a visual indicator that the spray is being uniformly applied to the cooking surface. There is no disclosure or suggestion of a directly ingestible stable foam product capable of yielding repeatable, measurable quantities of an active agent from an aerosol container.

Other disclosures of vegetable oil, lecithin-containing edible aerosols (U.S. Pat. Nos. 4,188,412 and 3,821,007) also indicate that such materials are sprays rather than foams. These patents additionally teach that foaming action would be undesirable in such a product.

U.S. Pat. No. 4,174,295 teaches the preparation of a pharmaceutical aerosol containing glycerides or monostearates.

SUMMARY OF THE DISCLOSURE

It has now been found that a stable, edible, anhydrous aerosol foam or whip capable of suspending up to 50% by weight of a dispersed solid can be prepared from a foamable, edible anhydrous liquid oil; a foaming agent; at least 15% by weight of dispersed solids; and controlled amounts of a food grade propellant which are sufficient to produce a stable foam rather than a spray. The foam, as delivered from an aerosol canister, has the consistency of whipped cream, is stable for extended periods and is hostile to the growth of micro-organisms so that refrigeration is not required. It can be safely ingested so that it is ideal as a carrier for active agents, especially oily or oil-soluble medicines, vitamins, minerals or other therapeutic agents. The foam of this invention assists in masking the taste of bitter drugs, such as phenylpropanolamine base, dyclonine base, steroids, etc. and making it easier to administer large amounts of high dosage medications such as fish oil supplements, castor oil and mineral oil. Such oils in a whip or aerosol foam becomes extremely palatable and easy to swallow, making it possible to prepare products containing a much larger amount of active ingredients, so that greater effectiveness and compliance can be achieved than is common with conventional therapeutic forms. For example, a typical dose of fish oil supplement is 6 one-gram soft gelatin capsules, whereas the foam of the invention requires only 2 rounded teaspoonfuls to deliver the same amount of active ingredient. Similar desirable results can be achieved with antitussives such as dextromethorphan base, antihistamines such as chlorpheniramine base, decongestants such as pseudoephedrine base and local anesthetics such as benzocaine or dyclonine base.

The stability of the novel foam formulation enables it to be controlled in the sense that it can be measured on a spoon or a similar device for oral administration, or measured into an applicator for rectal or vaginal administration. Obviously, such a foam is capable of being packaged in small, portable aerosol containers (the size of a typical breath spray container) which may be easily transported in a pocket or purse as well as in shaving cream-sized containers for home use.

The stability of the whip or foam product also enables the present invention to be utilized as a base for food products. Thus, it can be combined with numerous sweetening and flavoring agents to provide a whipped cream-type food product which needs no refrigeration and no preservatives. Sweetening and flavoring agents, of course, may also be employed to enhance the flavor of pharmaceutical products to further enhance the likelihood of patient compliance.

While not wishing to be limited to any particular theory, it is believed that the formulations of the present invention are capable of achieving the foregoing results without valve clogging due to a novel combination of ingredients that produces a high viscosity formulation capable of keeping the small solids particles dispersed and of lubricating the aerosol valve.

In a preferred embodiment of the present invention, the propellant comprises 1 to 10 wt. % of the composition, the foaming agent comprises 2 to 40 wt. %, the solid particles comprise at least 15 wt. % and are insoluble in the other ingredients of the composition, and the balance of the composition is the liquid oil.

Typically the propellant is a hydrocarbon, preferably propane. The foaming agent is selected from the group consisting of lecithin, polyglycerol esters of fatty acids having an HLB (hydrophilic/lipophilic balance) value of between 4.0 and 13.0, glycerol esters of fatty acids having an HLB value of between 2.5 and 4.5, sorbitan esters of fatty acids having an HLB value of between 3.0 and 7.0 and mixtures therof. The solid particles are active agents selected from the group consisting of powdered skim milk, crushed nut solids, powdered flavors, sugars, sugarless sweeteners, and clays, with powdered sugar being a preferred solid particle. The solid particles are insoluble in the other ingredients of the foam composition and have an average size in the range of 50 to 100 microns.

The liquid oil may be a non-therapeutic agent selected from the group consisting of soybean oil, partially hydrogenated soybean oil, linseed oil, corn oil, peanut oil, sunflower oil, cottonseed oil, olive oil, liquid petrolatums, oleic acids, lauric acids and mono- and diglyceride oils, or it may be an active therapeutic agent selected from the group consisting of mineral oil, castor oil, fish liver oils, fish body oils, and various oil-soluble ingredients such as epinephrine, isoproterenol, phenylpropanolamine base, ephedrine, amphetamine, dibucaine, dyclonine base, lidocaine, chloral hydrate, benzyl benzoate, vitamins, and steroid hormones.

The present invention also encompasses, as an article of manufacture, a pressurized aerosol container, the container having therein an edible, anhydrous aerosol foam composition. The composition comprises a foamable liquid oil, a foaming agent and a propellant, the propellant being present in an amount sufficient to produce a stable, measurable foam but insufficient to produce a spray when the composition is ejected through an aerosol valve, and at least 15% by weight of dispersed solid particles.

DETAILED DESCRIPTION OF THE PREFERRED EMBODIMENTS

The essential components of the present invention are:
1. A foamable, edible, anhydrous liquid oil.
2. A foaming agent (surfactant system).
3. At least a 15% concentration by weight of dispersed solids.
4. A food grade propellant.

THE LIQUID OIL

The liquid oil can be the sole active agent of the system, as in the case of fish oil or mineral oil, or can be the carrier for an oil-soluble active agent, as in the case of oil-soluble vitamins or oil-soluble therapeutic agents. As used throughout the specification, the term "oils" includes "oil-soluble active agents".

The foamable, edible anhydrous liquid oils utilized in the present invention are varied and of no great critical significance except where they are themselves the active agents. Typical among the edible organic oils useful for the present invention are those such as soybean oil, partially hydrogenated soybean oil, vegetable oil, linseed oil, corn oil, peanut oil, sunflower oil, cottonseed oil, olive oil, liquid petrolatum, oleic acid, lauric acid, and mono- and diglyceride oils. As indicated above, the basic criteria for a liquid oil utilizable in the present invention is that it is foamable and edible.

Typically, the edible oils utilized in the present invention are present in the formulation in a percentage of 35 to 75% by weight of the total composition. A preferred range is 45 to 70% by weight of the total composition. The amount of oil may be varied based upon the nature and amount of the other ingredients in the formulation, such as the amount of dispersed solids. Ordinarily, the percentage amount of each other ingredient in the formulation is first selected, and the oil is the ingredient added to bring the formulation to 100%.

The present invention provides a valuable delivery system for the oral administration of oily medicinal agents such as the following: mineral oil as a lubricant laxative, castor oil as an irritant laxative, cod liver and other fish liver oils as natural sources of vitamins A and D, fish body oils containing Omega 3 fatty acids as blood cholesterol reducers for the prevention of heart attacks, oil-soluble vitamins (such as vitamins A, D, E, and K), oil-soluble therapeutic agents (such as steroid hormones, e.g. estradiol, testosterone, progesterone, cortisone and hydrocortisone), sympathomimetics (such as epinephrine, isoproterenol, phenylpropanolamine, ephedrine, and amphetamine), anesthetics (such as dibucaine, dyclonine, and lidocaine), sedatives (such as chloral hydrate), anthelmintics (such as benzyl benzoate), and other oil-soluble medicinal agents. The active pharmaceutical materials in oil form which can be incorporated in the foam of the present invention can be any of the common analgesics, antitussives, laxatives, vitamins, minerals, or any other type of therapeutic agent. Indeed, most therapeutic agents which are normally in a water-soluble solid particle form (e.g., dyclonine, phenylpropanolamine) can be converted to oil-soluble amine bases and incorporated as such in the foams of the present invention.

In addition to serving as a vehicle for active agents for therapeutic (including nutritional supplement) purposes, it has been found that the systems of this invention can be used to prepare excellent tasting food products. Food products that normally require refrigeration, to prevent dry out and spoilage due to air oxidation, can be prepared in this system with extended shelf life, requiring no refrigeration or protection from the atmosphere. Such shelf-stable food products having active oil ingredients include dressings for salads and bread toppings (such as peanut butter and garlic butter), dessert foam and mousse toppings, coffee creamers, etc.

This novel system permits the preparation of unique products that solve the significant problem of the stability of oils (or oil-soluble active agents) that are vulnerable to oxidation. Since oxygen can easily be excluded from the system in the aerosol can, the integrity of oils such as fish oil containing Omega 3 fatty acids can be preserved. Similarly, cod liver oil and other fish liver oils can be maintained for long periods of time without loss in vitamin potency or oxidation of their unsaturated fatty acids. Oil-soluble vitamins can be dissolved in the oils in these systems and their potency can be maintained over the shelf life of such products.

THE FOAMING AGENT

Foaming agents utilizable in the present invention are selected from the group consisting of lecithin and various polyol fatty acid esters and mixtures thereof. Lecithin is the commercial name for a class of naturally occurring compounds derived from soybeans. These compounds are phosphatides and phospholipids. The principal components of lecithin are a naturally occurring mixture of phosphatidyl choline, phosphatidyl ethanolamine, inositol phosphatides and related phosphorous containing lipids. Chemically, lecithin is described as phosphatidyl choline and is a mixture of the diglycerides of stearic, palmitic and oleic acids linked to the choline ester of phosphoric acid. It is available commercially as a 60% solution in soybean oil or as a granular powder essentially free of soybean oil. A hydroxylated lecithin, modified to increase the hydrophilic properties is also commercially available. This hydroxylated lecithin is commonly supplied as a 60% solution in soybean oil.

The polyol fatty acid esters utilizable in the present invention are commercial products and are comprised of three types:

1. Glycerol esters of fatty acids.
2. Polyglycerol esters of fatty acids.
3. Sorbitan esters of fatty acids.

The glycerol esters which have been found to be advantageous in generating a suitable anhydrous edible aerosol foam are prepared by standard esterification methods and have an HLB of between 2.5 and 4.5. Among the preferable glycerol fatty esters utilizable in the present invention are those such as glycerol monostearate (HLB 3.2) and glycerol monooleate (HLB 3.4).

The polyglycerol esters utilizable in the present invention are commercial products prepared by first polymerizing glycerine under alkaline conditions. The polymerization is controlled to yield the particular desired average molecular weight. Investigations indicate that the polymerization of glycerol progresses predominately in a straight-chain manner. The esters are prepared by reacting the polyglycerols with a specific fatty acid or by the alcoholysis of a triglyceride. by this method, it is possible to prepare esters ranging anywhere from hydrophilic monoesters such as decaglycerol monolaurate to a lipophilic decaglycerol decaoleate.

The polyglycerol esters preferably used in the present invention have an HLB value of between 4.0 and 13.0. These have been found to be most advantageous in generating a suitable anhydrous aerosol foam. Among the preferable polyglycerol esters utilizable in the present invention are those such as: hexaglycerol distearate (HLB 4.0), decaglycerol tetraoleate (HLB 6.0), triglycerol monostearate (HLB 7.0), triglycerol monooleate (HLB 7.0), octaglycerol monostearate (HLB 12.0) and octaglycerol monooleate (HLB 13.0).

The sorbitan fatty acid esters which have been found to be advantageous in generating a suitable anhydrous edible aerosol foam are commercial products prepared by standard esterification methods and have an HLB of between 3.0 and 7.0. Among the preferable sorbitan esters utilizable in the present invention are those such as sorbitan monostearate (HLB 4.7), sorbitan monooleate (HLB 4.3), and sorbitan monopalmitate (HLB 6.7).

Additionally, a combination of any of the polyol fatty acid esters may be utilized in the present invention.

The polyol fatty acid esters are somewhat more hydrophilic than lecithin so that their use allows the foamable, edible anhydrous liquid oil to be more easily dispersed when contacted with an aqueous medium. This gives a much less oily feel in the mouth and releases the suspended medicament more rapidly in the stomach. Additionally, they may be used in conjunction with lecithin in the same system which causes the lecithin to become more hydrophilic and therefore more palatable than the lecithin alone. This combination also causes the release of an active agent—whether oil or solid—faster in the stomach. As it is necessary for the final product to be edible, the polyol esters are approved for internal use by the Food and Drug Administration.

The foaming agent utilized in the present invention is present in an amount of from 2 to 40% by weight. The amount of foaming agent utilized depends upon the particular foaming agent being utilized, the particular foamable, edible, anhydrous liquid oil being utilized and the propellant system. A preferred range of foaming agent is from about 3 to 15% by weight of the composition, with 10% being especially preferred. It is a particularly desirable additional feature of the foaming agents that they possess surfactant properties and, therefore, affect the rate at which the active ingredient of the foam—whether oil or dispersed solid—is released in the mouth. Accordingly, some variations in the amount of foaming agent in a particular formulation may be purposely chosen based on the nature of the active ingredient in order to control the rate of release.

THE PROPELLANT

The edible propellant can be selected from the class of hydrocarbons that are gaseous under atmospheric pressures and liquefy when compressed, or certain edible fluorocarbons such as FREON 115. The most commonly used are propane, butane and isobutane. Propane is approved for use in ingested products and can be obtained commercially in an odorless and tasteless form which is ideally suited for use in preparing the whip of the present invention. Since these liquefied gases are soluble in the oil vehicle of the composition, there is a resulting reduction in their vapor pressure. Therefore, it is most advantageous to use propane since it has the highest pressure of the three generally available hydrocarbon propellants and, even when dissolved in the low concentrations normally employed in this invention, produces a product with a pressure of 30-40 pounds per square inch over atmospheric pressure. This pressure is required to eject the foam from the container and produce a stable, dense foam which can be measured onto a spoon to facilitate administration. However, since propane is soluble in the oil base, there is very little pressure drop from the first to the last actuation of the aerosol valve and a satisfactory foam is produced when each dose is expelled.

The amount of propellant used is critical since too much will produce an undesirable spray rather than the desired stable, measurable foam. Amounts of propellant in the range of from 1-10 wt. % are operative, but 3-5 wt. % is the preferred concentration based upon the total weight of the contents of the aerosol container. The amount of propellant used may vary somewhat, depending upon the nature and amount of the other ingredients in the composition but, in all cases, the lowest amount sufficient to form a stable, measurable foam without forming an unmeasurable spray will be selected.

Propellants other than the liquefied hydrocarbon gases can be used including compressed gases like the edible fluorocarbons (e.g., Freon 115), nitrogen, nitrous oxide and carbon dioxide, although they do not produce the most desirable foams over the life of the product in use.

THE DISPERSED SOLIDS

A particularly important and surprising feature of the foams of this invention is their ability to suspend high concentrations, i.e., up to 50% by weight, of solids, and mask their taste upon ingestion of the foam. Preferably, the suspended particles are ground to a very fine particle size since this facilitates the formation and maintenance of a uniform dispersion and prevents clogging. Particle sizes in the range of 50 to 100 microns in diameter are preferred.

The foam of the present invention will contain at least 15 wt. % of suspended solid particles and can contain up to 50 wt. % of suspended solid particles without any appreciable valve malfunctioning. This ability to suspend high percentages of solids without valve malfunctioning enables the aerosol foam system of the present invention to be utilized for a wide variety of formulations. The reasons for the unique ability of the foams to suspend such a high concentration of solids without valve clogging are not fully understood, but it is believed to result from a combination of the small particle size, the high viscosity of the foam formulation due to its low propellant content which aids in keeping the particles dispersed and reduces agglomeration and settling, and the lubricating effect of the oil on the valve.

These suspended solid particles serve to modify the taste characteristics of the oil to make it less greasy and also serve to make the foam more dense by their physical presence adding substance to the foam. They also serve as foci for evaporation of the propellant when exposed to the atmosphere upon expulsion from the aerosol can. This makes the foam more dense and physically stable in much the same way as meringues are made stable by beating air into egg whites or whipped cream is made stable by beating air into cream.

Powdered sugar is one of the preferred dispersed solids since it provides good taste and mouth feel characteristics to the foam, in addition to providing the beneficial physical effects described above. Sugars other than sucrose (such as fructose) or "sugarless" sweeteeners (such as sorbitol) can be employed. Other dispersed solids can also be used such as powdered skim milk for coffee creamers, the solids of crushed nuts (e.g., peanuts), clays (i.e., absorbents), lakes of colors (i.e., pigments), powdered flavors, etc., depending upon the needs of the specific product formulation. In all cases the particle size should be less than 100 microns to prevent clogging the valves of the aerosol.

The system of this invention can be used to prepare excellent tasting food products. Food products, such as whipped cream or whipped toppings that normally require refrigeration to prevent dry out or spoilage due to air oxidation, can be prepared in this system with extended shelf life, requiring no refrigeration or protection from the atmosphere. Such shelf-stable food products include toppings for desserts and ice cream (e.g., chocolate mousse or strawberry mousse) incorporating Bakers chocolate, vanillin and/or cocoa powder as dispersed solids, coffee or hot drink creamers (e.g., for instant cappuccino) incorporating powdered non-fat milk and titanium dioxide as dispersed solids, spreads (such as peanut butter) incorporating crushed nut solids as dispersed solids, etc.

The dispersed solids may be an adsorbent such as clay; for example, the clay adsorbent available under the mark Veegum F (composed of magnesium and aluminum silicates). Such adsorbents complex the distasteful active ingredients, such as phenylpropanolamine base or dextromethomorphan base, on their surface and prevent them from contacting the tastebuds of the mouth. The clays are especially useful in conjunction with other dispersed solids, such as sugars, which mask any residual taste of the distasteful ingredients.

The dispersed solids may be an exothermic agent such as anhydrous sodium aluminosilicate (commercially available under the name Valfor 950). Upon exposure to water the exothermic agent undergoes a heat-producing reaction capable of warming up the dispensed foam. A foam containing such an exothermic agent may find utility in a therapeutic setting where the heat may enhance the absorption of therapeutic agents in the foam by the body or simply as a self-heating massage lotion. While the useful exothermic agents are not particularly pleasant tasting, the composition can be given an acceptable taste through the use of sugars, flavorings, and the like as taught herein. The exothermic agent may be employed in a hot oil anti-dandruff mousse so that the application of the foam to wet hair generates heat, which promotes the penetration of the oils into the dandruff layers on the scalp, thereby aiding in their removal upon subsequent rinsing. The object in such a case is not to produce a particularly enjoyable flavor, but simply to provide a composition which is safe in the event that some of the mousse accidently enters the user's mouth and which is of generally tolerable taste such that the user does not have a strongly negative reaction to the taste.

GENERAL

The oily or greasy mouthfeel of the oils can be minimized and largely eliminated, so that the final taste of the product can be very pleasant, by the three other essential components of this unique system. The first method of reducing oiliness in the mouth is provided by the high concentrations of dispersed solids which the system of this invention can tolerate, and indeed requires. This effect is analogous to the taste difference that exists between shortening which is greasy and cake icing which is pleasant. The difference is that, in the case of icing, the shortening is mixed with large amounts of powdered sugar so that, when ingested, the sugar dissolves in the mouth and dilutes the greasy effect of the shortening. In the system of this invention large concentrations of sugar can be mixed with the oils to provide the same effect in the mouth.

The second method of reducing oiliness in the mouth is provided by the foaming agent, which is one or more edible surfactants. Since these surfactants modify the oils to make them more water-dispersible, it has been found that the system becomes more dispersible in the aqueous fluids in the mouth and this further reduces the greasy mouthfeel the oils normally possess. And since we have found that it is possible to adjust this effect by increasing the water-dispersibility of the surfactant system, an even greater reduction in greasiness in the mouth can be effected.

The third method of reducing oiliness in the mouth is provided by the edible propellant, which is an essential component of the system. Since the propellant causes the composition to expand and foam when it is expelled from the aerosol can, the density of the product is greatly reduced. In fact the density changes from about 1.0 g/cc in the can to about 0.25 g/cc when the foam is formed upon expulsion from the can. This fourfold reduction in density (or increase in volume for a given weight of product) provides a further dilution of the oil in the product so that greasiness is even further reduced upon ingestion.

Thus the system provides three ways to reduce oiliness or greasiness of oils upon ingestion—dispersed solids to overcome the flavor of the oily taste, surfactants to disperse the oil in the mouth, and propellant to reduce the density of the oil.

Since the system of this invention is completely anhydrous, it provides a very poor medium for the growth of microorganisms. And if sugar is used as one or all of the dispersed solids, it has been found that the system is actively bactericidal. This surprising effect was discovered when formulations of this invention were deliberately inoculated with aqueous suspensions of microorganisms. It was expected that these organisms would not grow in the medium of the product. But it was found that the organisms were killed in the product, even though no chemical preservative was present. This effect was found with all the organisms used, even pathogenic anaerobes like Clostridium which could be expected to remain viable in systems where air was excluded. The system of this invention was found to be cidal in these organisms so that within a week the number of organisms present was reduced to substantially zero. This cidal effect means that contamination by microorganisms during the manufacture of this product is unlikely. In addition, the product that remains in the spout of the aerosol can during use by the consumer will not be contaminated by organisms from the environment.

It will be appreciated that the present invention includes systems in which the active ingredient is either an oil or a dispersed solid, and the active agent, if also therapeutic, is an oil. This system thus permits the formulation of both oils (including oil-soluble materials) and solids as active agents into products that are stable when on the shelf, stable during use by the consumer, and pleasant to take when ingested.

The foams of the present invention are prepared by conventional formulating techniques. Thus, typically, the foamable edible anhydrous liquid oil and the foaming agent are mixed together along with any other soluble ingredients of the composition. The solid to be dispersed is then added, and the resultant mixture passes through an appropriate mill to ensure uniform particle size. The batch is then submitted for aerosol filling into an aerosol can. An aerosol valve is placed on the can and crimped onto the can. The food grade propellant is then added by pressure filling.

In addition to the essential ingredients of the foam, there may also be incorporated in the foams of the present invention any of a variety of additives or a combination thereof, commonly added to aerosol compositions or to toiletries, cosmetics, or pharmaceuticals. Typically, such additives are those such as emollients, lubricants, humectants, abrasives, and perfumes. Thus, the edible anhydrous aerosol foam of the present invention may be used as a vehicle for any of a large variety of active pharmaceutical materials or cosmetic ingredients. Additionally, the foam itself can be used as a base for various sweetening and flavoring agents in order to provide a food item.

EXAMPLES

In all of the following examples high levels of solids are dispersed in oils and foamed with surfactant and propellant from the aerosol can. All parts are by weight, unless otherwise indicated.

Unless otherwise indicated, each formulation of the examples was prepared according to the following general instructions: Heat the oils, the surfactants, and any other oil-soluble ingredients together to 60° C.±5° C. Then add the solids to the oil phase with vigorous agitation to assure uniform dispersion (5–15 minutes). After cooling to 40° C.±5° C., add any flavors and mix well. Pass the composition through a homogenizer or colloid mill to disperse agglomerates. Fill an aerosol can with the composition and then crimp on a valve. Add the propellant (e.g., propane) through the valve. Shake well to dissolve the propellant in the system.

EXAMPLE I

Fish Oil Whip

|  | Weight % |
|---|---|
| Fish Oil-30% Omega 3 fatty acids (oil) | 53.80 |
| Octaglycerol monooleate (foamer) | 4.00 |
| Triglycerol monooleate (foamer) | 4.00 |
| Sorbitan monostearate (foamer) | 3.00 |
| Cab-O-Sil M5 (anti-caking agent, fumed SiO2, (dispersed solids) | 1.50 |
| Citric acid anhydrous USP (tartness) | 0.15 |
| Flavors (oil-solubles) | 0.55 |
| Sugar 12X, N.F. (sweetener, dispersed solids) | 30.00 |
| Propane (propellant) | 3.00 |
|  | 100.00 |

This system masks the taste of the fish oil and stabilizes the oil against rancidification due to air oxidation or microbial attack. Each five gram spoonful of the delicious whip delivers about three grams of fish oil, equivalent to taking three large difficult-to-swallow soft gelatin capsules.

EXAMPLE II

Cod Liver Oil Whip

|  | Weight % |
|---|---|
| Cod liver oil USP | 44.80 |
| Decaglycerol tetraoleate | 6.00 |
| Sorbitan monostearate | 2.00 |
| Glyceryl monostearate | 2.00 |
| Sugar 12X, N.F. | 40.00 |
| Citric acid | 0.15 |
| Cab-O-Sil M5 | 1.50 |
| Flavors | 0.55 |
| Propane | 3.00 |
|  | 100.00 |

The formulation effectively masks the taste and odor of cod liver oil and provides a palatable cream whip form for the administration of this natural source of vitamins A and D, particularly to children.

EXAMPLE III

Chocolate Dessert Foam Topping

|  | Weight % |
|---|---|
| Lecithin, granular | 5.00 |
| Sugar, 12X, N.F. | 20.00 |
| Bakers chocolate (dispersed solid) | 4.00 |
| Glyceryl monostearate | 2.50 |
| Vanillin (dispersed solid) | 0.25 |
| Flavor | 0.40 |

-continued

|  | Weight % |
|---|---|
| Soybean oil | 64.85 |
| Propane | 3.00 |
|  | 100.00 |

This system delivers a delicious chocolate topping for ice cream cakes and for other desserts. As it requires no refrigeration, it can be kept in convenient locations in the kitchen or dining room.

EXAMPLE IV

Mineral Oil Laxative Foam

|  | Weight % |
|---|---|
| Heavy mineral oil, USP | 55.2 |
| Sugar 12X, N.F. | 30.0 |
| Cab-O-Sil M5 | 3.0 |
| Veegum F (absorbent, dispersed solid) | 2.0 |
| Triglycerol monostearate | 3.0 |
| Sorbitan monostearate | 3.5 |
| Citric acid anhydrous USP | 0.1 |
| Orange flavor | 0.2 |
| Propane | 3.0 |
|  | 100.00 |

One ounce of whip provides a laxative dose of mineral oil for adults in a very pleasant, non-greasy, easy-to-take form.

EXAMPLE V

Chocolate Mousse Topping

|  | Weight % |
|---|---|
| Decaglycerol tetraoleate | 6.0 |
| Lecithin | 2.0 |
| Sorbitan monostearate | 2.0 |
| Soybean oil | 50.4 |
| Sugar 12X N.F. | 25.0 |
| Cocoa, powdered (dispersed solids) | 10.0 |
| Cab-O-Sil M5 | 1.0 |
| Artificial chocolate flavor (oil-soluble) | 0.6 |
| Propane | 3.0 |
|  | 100.0 |

This whip can be used as a cake frosting or topping for desserts. The aerosol form facilitates spreading. No refrigeration is required.

EXAMPLE VI

Coffee Creamer

|  | Weight % |
|---|---|
| Powdered nonfat milk (dispersed solids) | 20.0 |
| Octaglycerol monooleate | 7.0 |
| Sorbitan monostearate | 2.0 |
| Cab-O-Sil M5 | 1.0 |
| Titanium dioxide (dispersed solids) | 1.0 |
| Mono and diglycerides of fatty acids (oils) | 5.0 |
| Flavors | 0.5 |
| Soybean oil | 59.5 |
| Propane | 4.0 |
|  | 100.0 |

This milk-containing coffee creamer tastes as good as cream and requires no refrigeration. It creates "instant cappuccino" with push-button ease.

EXAMPLE VII

Castor Oil Whip

|  | Weight % |
| --- | --- |
| Castor oil, USP | 56.30 |
| Sugar 12X, N.F. | 30.00 |
| Decaglycerol monooleate | 6.00 |
| Sorbitan monostearate | 2.00 |
| Cab-O-Sil M5 | 1.00 |
| Citric acid, anhydrous USP | 0.15 |
| Flavors | 0.55 |
| Propane | 4.00 |
|  | 100.00 |

This good tasting foam makes it easier and more convenient for the patient to ingest the large quantity of castor oil required for intestinal purging prior to colonic X-rays or other diagnostic testing.

EXAMPLE VIII

Vitamin E Whip

|  | Weight % |
| --- | --- |
| Vitamin E (Alpha tocopherol) 1,000,000 IU per gram (oil soluble) | 0.1 |
| Soybean Oil | 44.6 |
| Sugar 12X, N.F. | 40.00 |
| Octaglycerol monooleate | 4.0 |
| Triglycerol monooleate | 4.0 |
| Sorbitan monostearate | 3.0 |
| Cab-O-Sil M5 | 1.0 |
| Flavors | 0.3 |
| Propane | 3.0 |
|  | 100.0 |

Each gram of whip contains 1,000 IU Vitamin E

Large doses of oil-soluble vitamins can be easily administered in whip form without requiring the swallowing of large capsules. Other vitamins or other nutritional supplements like lecithin can be added easily to the system. The stability of all these ingredients is assured by the inert atmosphere and the hermetic seal of the aerosol form.

EXAMPLE IX

Dyclonine Sore Throat Whip

|  | Weight % |
| --- | --- |
| Dyclonine, base (oil-soluble) | 0.1 |
| Menthol | 0.2 |
| Sugar 12X, N.F. | 30.0 |
| Cab-O-Sil M5 | 1.5 |
| Flavors | 0.3 |
| Soybean oil | 56.4 |
| Decaglycerol tetraoleate | 6.0 |
| Sorbitan monostearate | 3.0 |
| Propane | 3.0 |
|  | 100.0 |

When local anesthetics like dyclonine are administered in whip form, they coat the back of the throat providing long lasting pain relief with minimal numbing of the mouth and tongue. This is in contrast to the general mouth-numbing effect produced by anesthetic lozenges or sprays.

EXAMPLE X

Phenylpropanolamine Whip

|  | Weight % |
| --- | --- |
| Phenylpropanolamine, base (oil-soluble) | 0.8 |
| Sugar 12X, N.F. | 25.0 |
| Veegum F | 2.0 |
| Cab-O-Sil M5 | 1.0 |
| Decaglycerol tetraoleate | 6.0 |
| Sorbitan monostearate | 4.0 |
| Soybean oil | 58.2 |
| Propane | 3.0 |
|  | 100.0 |

Each 3 gram dose contains 25 mg of phenylpropanolamine.

Amine bases like phenylpropanolamine are soluble in the oil system and can be reliably and accurately administered by means of a metered valve. In this system the clay (Veegum F) is used to complex with the drug and eliminate its bitter taste.

EXAMPLE XI

Chocolate Mousse Foam Food Topping

|  | Weight % |
| --- | --- |
| Lecithin, granular | 5.00 |
| Sugar, fine powder 10X | 20.00 |
| Bakers chocolate | 4.00 |
| Glycerol monostearate | 2.50 |
| Vanillin | 0.25 |
| Flavor | 0.40 |
| Soybean oil | 64.85 |
| Propane | 3.00 |
|  | 100.00% |

Procedure:

The lecithin, glycerol monostearate, and soybean oil are heated to 150° F. until clear and uniform. The vanillin and Bakers chocolate are mixed in, and the batch cooled to room temperature. The sugar and flavor are added, and the entire batch passed through a suitable mill to ensure particle uniformity. The batch is then submitted for aerosol filling. Because the sugar is suspended in the batch, the aerosol can must be shaken before use. When the contents are used, a good tasting whipped cream-like foam is formed.

EXAMPLE XII

Hot Oil Anti-Dandruff Mousse

|  | Weight % |
| --- | --- |
| Valfor 950(anhydrous sodium aluminosilicate) | 35.00 |
| Cab-O-Sil M5 | 1.00 |
| Sorbitan monostearate | 4.00 |
| Polyethylene glycol 400 dioleate | 2.00 |
| Soybean oil, partially hydrogenated | 52.50 |
| Fragrance | 0.50 |
| Propane | 5.00 |
|  | 100.0 |

When this foam is applied to the wet hair and scalp, heat is generated as a result of the exothermic reaction between Valfor 950 and water. The heat promotes the penetration of the oils into the dandruff layers on the scalp, aiding in their removal by subsequent rinsing.

The foam is ingestible and palatable, although not particularly appetizing.

It will be apparent to those skilled in the art that many modifications, both of materials and methods, may be practiced without departing from the purpose and intent of the disclosure.

What is claimed is:

1. An edible, anhydrous aerosol foam composition comprising a foamable liquid oil, a foaming agent, a propellant, and dispersed solid particles, said propellant being present in an amount sufficient to produce a stable, measurable foam but insufficient to produce a spray when said composition is ejected through an aerosol valve, and said dispersed solid particles being at least 15% by weight of said composition.

2. The composition of claim 1 wherein said propellant comprises 1 to 10 wt. % of said composition.

3. The composition of claim 1 wherein said propellant is a hydrocarbon.

4. The composition of claim 3 wherein said propellant is propane.

5. The composition of claim 1 wherein said solid particles are insoluble in the other ingredients of said foam composition.

6. The composition of claim 1 wherein the average size of said solid particles is in the range of 50 to 100 microns.

7. The composition of claim 1 wherein said solid particles are selected from the group consisting of powdered skim milk, crushed nut solids, powdered flavors, sugars, sugarless sweeteners, and clays.

8. The composition of claim 7 wherein said solid particles comprise powdered sugar.

9. The composition of claim 1 wherein said solid particles comprise an exothermic agent.

10. The composition of claim 1 wherein said foaming agent is selected from the group consisting of lecithin, polyglycerol esters of fatty acids having an HLB value of between 4.0 and 13.0, glycerol esters of fatty acids having an HLB vaue of between 2.5 and 4.5, sorbitan esters of fatty acids having an HLB value of between 3.0 and 7.0 and mixtures thereof.

11. The composition of claim 9 wherein said foaming agent comprises 2 to 40 wt. % of said composition.

12. The composition of claim 1 wherein said foaming agent is substantially comprised of at least one water-dispersible surfactant.

13. The composition of claim 1 wherein at least one of said liquid oil and said solid particles comprises an active non-therapeutic agent.

14. The composition of claim 1 wherein said liquid oil comprises an active therapeutic agent.

15. The composition of claim 14 wherein said liquid oil is selected from the group consisting of mineral oil, castor oil, fish liver oils, fish body oils, and oil-soluble materials selected from the group consisting of epinephrine, isoproterenol, phenylpropanolamine base, ephedrine, amphetamine, dibucaine, dyclonine base, lidocaine, chloral hydrate, benzyl benzoate, vitamins, and steroid hormones.

16. The composition of claim 1 wherein said liquid oil is selected from the group consisting of soybean oil, partially hydrogenated soybean oil, linseed oil, corn oil, peanut oil, sunflower oil, cottonseed oil, olive oil, liquid petrolatums, oleic acids, lauric acids and mono- and diglyceride oils.

17. The composition of claim 1 wherein said propellant comprises 1 to 10 wt. % of said composition, said foaming agent comprises 2 to 40 wt. % of said composition, said solid particles comprise at least 15 wt. % of said composition and are insoluble in the other ingredients of said foam composition, and the balance of said composition is said liquid oil.

18. As an article of manufacture, a pressurized aerosol container, said container having therein an edible, anhydrous aerosol foam composition comprising a foamable liquid oil, a foaming agent, a propellant, said propellant being present in an amount sufficient to produce a stable, measurable foam but insufficient to produce a spray when said composition is ejected through an aerosol valve, and at least 15% by weight of dispersed solid particles.

* * * * *